(12) United States Patent
Sumanaweera

(10) Patent No.: US 6,475,149 B1
(45) Date of Patent: Nov. 5, 2002

(54) BORDER DETECTION METHOD AND SYSTEM

(75) Inventor: Thilaka Sumanaweera, San Jose, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/960,461

(22) Filed: Sep. 21, 2001

(51) Int. Cl.[7] ................................. A61B 8/00
(52) U.S. Cl. ........................ 600/441; 600/443
(58) Field of Search ..................... 600/440, 441, 600/443, 447, 453–456; 128/916

(56) References Cited

U.S. PATENT DOCUMENTS

| | | | |
|---|---|---|---|
| 5,669,387 A | * 9/1997 | Mine | 600/441 |
| 5,735,797 A | * 4/1998 | Muzilla | 600/455 |
| 5,857,973 A | * 1/1999 | Ma et al. | 600/441 |
| 5,860,924 A | * 1/1999 | Quistgaard | 600/441 |
| 5,957,138 A | * 9/1999 | Lin et al. | 600/453 |
| 5,967,987 A | 10/1999 | Sumanaweera et al. | |
| 6,068,598 A | 5/2000 | Pan et al. | |
| 6,086,539 A | 7/2000 | Guracar et al. | |
| 6,106,465 A | 8/2000 | Napolitano et al. | |
| 6,190,321 B1 | 2/2001 | Pang et al. | |

OTHER PUBLICATIONS

John Canny, "A Computational Approach to Edge Detection," Nov. 1986, pp. 679–698.

* cited by examiner

*Primary Examiner*—Francis J. Jaworski

(57) ABSTRACT

Vessel border detection is provided. A top border or border closer to a transducer of a vessel is detected using Doppler data. Since little flowing fluid is provided between the top border of the vessel and the transducer, reverberation artifacts are minimized. A bottom border or border of the vessel farther from the transducer is detected from B-mode data. Since few tissue layers are provided immediately adjacent the bottom border between the bottom border and the transducer, reverberation artifacts are minimized. The detected borders are used for further calculation or display, such as automatically estimating vessel diameter for endothelial function assessment. In alternate embodiments, different techniques for identifying fluid or tissue data are used, such as magnetic resonance imaging, CAT scan, x-ray or other techniques for imaging interior portions of a patient. Borders for other fluid regions in a patient may be detected, such as a heart border or other organ borders.

20 Claims, 1 Drawing Sheet

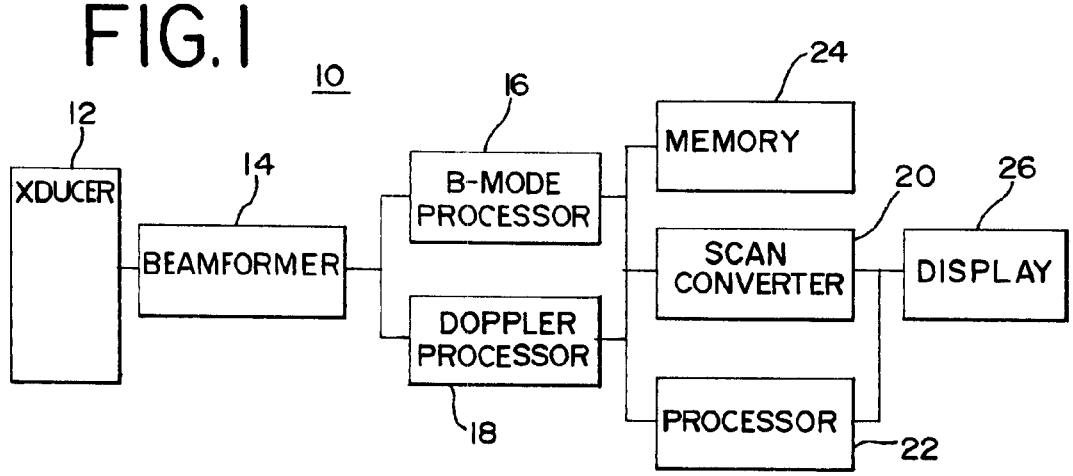
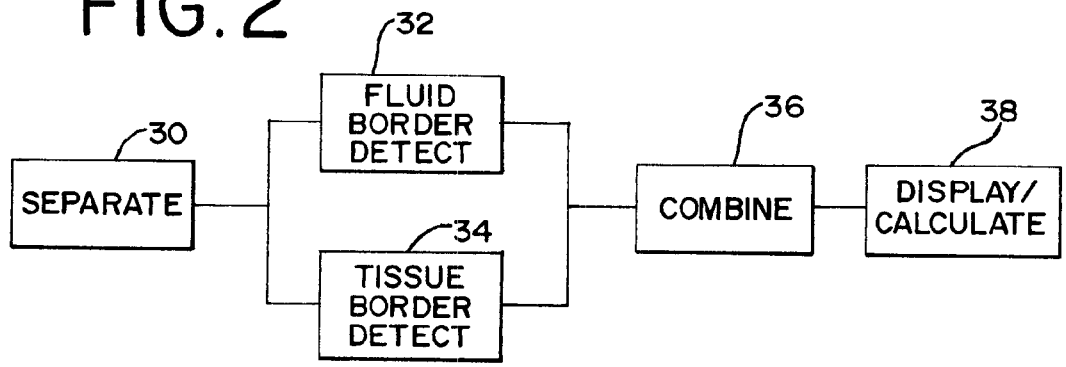
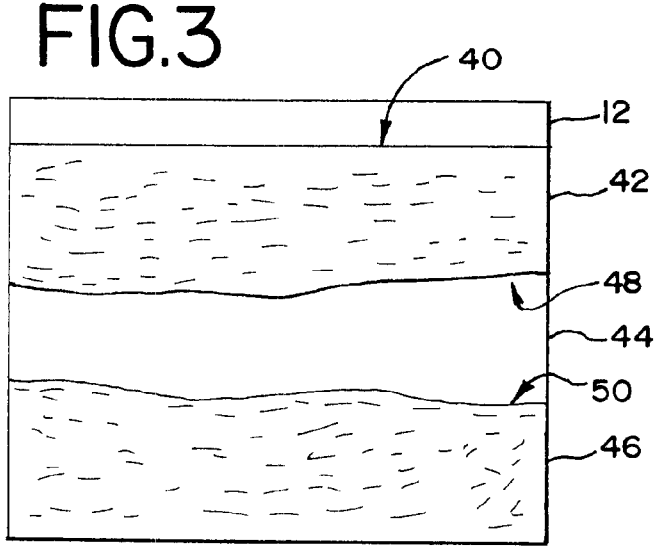

BORDER DETECTION METHOD AND SYSTEM

BACKGROUND

This invention relates to border detection. In particular, organ or vessel boundaries in a patient or animal are detected.

In ultrasound imaging, detecting the borders of a vessel assists in diagnosis. Medical diagnosis by a doctor may be assisted by an image showing vessel boundaries. Volume flow or other calculations are based on the diameter of a vessel. Typically, B-mode imaging is used for identifying borders. Due to reverberation of ultrasound energy from multiple tissue layers, borders may not be well defined. For example, the border of the vessel closest to the transducer appears fuzzy or is poorly defined due to reverberations from tissue layers adjacent to the border. The border of the vessel furthest from the transducer is more sharply defined since few or no tissue layers are provided immediately adjacent the border between the border and the transducer.

To better define a border, manual border editing is provided. Using a track ball or other pointing device, a user traces where the user expects that a border is located. However, manual border editing is time-consuming and may be inaccurate. For diagnosis at different times or locations, border detection using manual techniques may be unrepeatable.

BRIEF SUMMARY

The present invention is defined by the following claims, and nothing in this section should be taken as a limitation on those claims. By way of introduction, the preferred embodiments described below include methods and systems for border detection. A border of a vessel closest to the transducer is detected using Doppler data. Since little flowing fluid is provided between the top border of the vessel and the transducer, reverberation artifacts are minimized. A border of the vessel farthest from the transducer is detected from B-mode data. Since few tissue layers are provided immediately adjacent the border farthest from the transducer between the border farthest from the transducer and the transducer, reverberation artifacts are minimized. The detected borders are used for further calculation or display. In alternate embodiments, different techniques for identifying fluid or tissue data are used, such as magnetic resonance imaging, CAT scan, x-ray or other techniques for imaging interior portions of a patient. Different ultrasound techniques may also be used, such as harmonic imaging, subharmonic imaging, multiple frequencies, coded excitation, Doppler tissue imaging or other techniques. Borders for other fluid regions in a patient may be detected, such as a heart border or other organ borders.

In a first aspect, a method for detecting a border associated with a fluid region is provided. A first portion of the border is detected with Doppler data. A second portion of the border is detected with B-mode data where the first and second portions of the border are different.

In a second aspect, a system for detecting a border associated with a fluid region of a patient is provided. A first processor is operable to detect first and second portions of the border associated with fluid and tissue data, respectively. A display is operable to display the first and second portions of the border.

In a third aspect, a method for detecting a border of a vessel is provided. The border of the vessel closer to the transducer is detected with flow data. The border of the vessel farther from the transducer is detected with tissue data.

Further aspects and advantages of the invention are discussed below in conjunction with the preferred embodiments.

BRIEF DESCRIPTION OF SEVERAL VIEWS OF THE DRAWINGS

The components in the figures are not necessarily to scale, emphasis instead being placed upon illustrating the principles of the invention. Moreover, in the figures, like reference numerals designate corresponding parts throughout the different views.

FIG. 1 is a block diagram of one embodiment of an ultrasound system for border detection.

FIG. 2 is a flow chart diagram representing one embodiment of a method for detecting borders.

FIG. 3 is a graphical representation of one embodiment of a region of a patient and an associated transducer.

DETAILED DESCRIPTION OF THE PREFERRED EMBODIMENTS

Both tissue and fluid data are used to detect vessel or organ borders. Fluid data, such as ultrasound Doppler data, more clearly or sharply identifies tissue-to-fluid borders, such as vessel borders closer to the transducer. Likewise, tissue data, such as ultrasound B-mode data, more clearly or sharply identifies fluid-to-tissue borders, such as vessel borders further away from the transducer. Since there is no moving blood flow or fluid flow above an upper or top portion of a vessel border, fewer reverberation artifacts are provided for Doppler data. Since there is minimal tissue adjacent to and closer to the transducer than the lower or bottom fluid border of the vessel, fewer reverberation artifacts for tissue data are provided. By combining border detection using two types of data, a well-defined border is detected for the entire fluid region, such as the vessel or organ.

FIG. 1 shows an ultrasound system 10 for border detection of vessels or organs. The system 10 includes a transducer 12, a beamformer 14, a B-mode processor 16, a Doppler processor 18, a scan converter 20, a processor 22, a memory 24, and a display 26. Additional, different, or fewer components may be provided. In one embodiment, the ultrasound system 10 comprises a 128 XP®, Aspen™, or Sequoia® ultrasound system manufactured by Acuson Corporation or a Allegra® ultrasound system manufactured by Siemens Medical Systems, Ultrasound Group. Other systems by the same or different manufacturers may be used. In alternative embodiments, MRI, CAT scan, X-ray or other systems for imaging the interior of a patient are used.

In alternative embodiments, the system 10 comprises a workstation, such as the Aegis workstation sold by Acuson Corporation. Image or other data is stored in a memory. A processor processes the data to detect a boundary. The data is acquired from another system or through the transfer of data from another device.

The transducer 12 comprises one-dimensional, 1.5 dimensional or two-dimensional arrays of PZT or CMUT elements. The transducer 12 includes a transmit surface for transmitting and receiving ultrasound energy into and from a patient or animal. The transmit surface corresponds to a flat or curved linear surface for one-dimensional arrays. A planar or curved planar surface is provided for multi-dimensional arrays. The transducer 12 flexibly connects to the remainder of the ultrasound system 10 so that the transducer 12 can be placed at different positions relative to the patient. The transducer 12 is adapted for use exterior or interior of the patient, such as catheter, endocavity, or intraoperative probes.

The beamformer 14 comprises analog or digital circuits for generating transmit waveforms and for focusing received ultrasound energy along one or more scan lines. The beamformer 14 outputs in-phase and quadrature or radio frequency data.

The B-mode processor 16 comprises one or more processors, digital signal processors, application specific integrated circuits, analog circuits, digital devices and combinations thereof. The B-mode processor 16 detects the magnitude, amplitude or intensity associated with received signals. B-mode data is responsive to tissue. B-mode or tissue data may be log compressed, filtered, or otherwise processed by the B-mode processor 16.

The Doppler processor 18 comprises one or more processors, digital signal processors, application specific integrated circuits, analog circuits, digital devices and combinations thereof. The Doppler processor 18 detects Doppler data representing flowing fluid. The Doppler data is obtained for a two-dimensional region of the patient. The Doppler processor 18 detects frequency shifts associated with the Doppler effect of moving or flowing fluid on the transmitted or received signals. The Doppler processor 18 includes a clutter filter for removing or reducing signals associated with tissue. The velocity, energy, or power, variance or combinations thereof are detected as flow or fluid data. Flow or fluid data may be detected using other processes and alternative embodiments, such as frequency analysis or non-ultrasound processes.

The processor 22 comprises one or more of a general processor, digital signal processor, application specific integrated circuit or combinations thereof. In one embodiment, the processor 22 comprises a general processor also used for controlling various components of the system 10 or other non-border detection processing. In alternative embodiments, the processor 22 comprises a dedicated processor or circuitry. In yet other alternative embodiments, the B-mode processor 16 and/or Doppler processor 18 perform the functions of the processor 22. The processor 22 detects borders from the Doppler and B-mode data. The processor 22 also combines the detected borders for performing various calculations or board display. The processor 22 may perform the calculations for display. For example, a volume flow is calculated as a function of the smallest diameter of the vessel or closest distance between two detected borders.

The scan converter 20 combines the Doppler and B-mode data and reformats the data for display or storage in a Cartesian display or other format. Alternatively, only B-mode, only Doppler or separate B-mode and Doppler data are formatted for display or storage. In one embodiment, the scan converter 20 formats the data as Digital Imaging And Communications In Medicine (DICOM) data for storage in the memory 24. The detected borders or associated calculations from the processor 22 are provided with the scan converted data to the display 26 or to the memory 24.

The display 26 comprises a flat panel, LCD or monitor for displaying an image. Displayed image includes tissue data, fluid data or combinations thereof. Detected borders and/or an associated calculation are also displayed.

The memory 24 comprises a RAM, system memory, CINE formatted memory, hard drive, disk drive, tape or other device for storing ultrasound, flow, fluid, tissue, B-mode, Doppler, DICOM, or other types of data representing a region of a patient. In one embodiment, ultrasound data is stored as image data combined from B-mode and Doppler data. In alternative embodiments, different types of data associated with the same region of the patient are stored separately. The memory 24 may also store detected border information. Alternatively, the processor 22 detects the border from the data stored in the memory 24 for generating an image on the display 26.

FIG. 2 shows a flow chart of one embodiment for detecting borders. After acquiring data, combined data is separated in act 30. Data associated with fluids is used for border detection in act 32, and data associated with tissue is used for border detection in act 34. The detected border information is combined in act 36. In act 38, the detected border is displayed or used for further calculations. The detected border comprises a one, two or three-dimensional border. Additional, different, or fewer acts may be provided.

The acquired data comprises combined data or separate data. Combined data includes tissue or flow data for each or a subset of the pixels associated with an image or a region of the patient. For example, B-mode and Doppler data are provided for each spatial location or pixel associated with a part of a DICOM or ultrasound image. As another example, one of B-mode or Doppler data is provided for each pixel or location within a scanned region of the patient.

For ultrasound data, the acquired data is responsive to the position of the transducer 12. FIG. 3 shows the transducer 12 positioned with the transmitting surface 40 adjacent to tissue 42 of a patient. The transducer 12 is positioned so that a vessel 44 is more parallel than perpendicular to the transmitting surface 40. As shown in FIG. 3, the vessel 44 is parallel with the transmitting surface 40 of the transducer 12. In alternative embodiments, the vessel 44 is at a greater angle to the transmitting surface 40. A top border 48 of the vessel 44 is closer to the transducer 12 than a bottom border 50. The bottom border 50 is further from the transducer 12 than the top border 48. As ultrasound energy transmitted from the transmit surface 40 travels away from the transducer 12, the energy passes through the tissue 42, to the tissue-to-fluid border 48, through the fluid within the vessel 44, to the fluid-to-tissue border 50 and finally passes into the tissue 46. Along the transmit path, some of the energy is reflected back towards the transducer 12.

In act 30, combined tissue and fluid data is separated. In one embodiment disclosed in U.S. Pat. No. 6,190,321, the disclosure of which is incorporated herein by reference, B-mode data is separated from Doppler data. First, the composite data is checked to determine whether the color Doppler image data included in the composite image is representative of Doppler velocity or Doppler energy. In this example, different algorithms are used to extract B-mode image data for these two different possibilities. This determination can be made from the header of the composite image file.

In act 32, fluid, flow or Doppler data is used to detect the border 48 of the vessel 44. Border detection identifies an ordered list of consecutively adjacent points or locations spaced along the vessel 44. A top portion or border 48 of the vessel 44 is detected. Given the path of transmitted energy away from the transducer 12, the border 48 associated with the tissue-to-fluid interface is detected using the Doppler data.

The border 48 is detected using one or more algorithms. In one embodiment, a gradient associated with the Doppler data is determined. For example, a Canny gradient detecting algorithm or software is used. (See Canny, J. "A Computational Approach to Edge Detection," IEEE PAMI 8 (6), pg. 679–698, Nov. 1986). A curve fitting algorithm determines a line associated with a maximum gradient. In alternative embodiments, a threshold is applied to the Doppler data. Spatial locations along a continuous line associated with values that exceed a threshold are identified. In yet other alternative embodiments, a Laplasian kernal is applied. In any of the various embodiments, a curve fitting algorithm may be applied so that a continuous border is identified. The border information may be filtered, such as low-pass filtered, to identify a smoother border 48.

The lower border 50 is detected from B-mode or tissue data in act 34. The lower border 50 of the vessel 44 corresponds to a fluid-to-tissue interface relative to a path of travel of ultrasound energy away from the transducer 12. The lower border 50 is detected from the tissue data using any of the algorithms discussed above for detecting the upper border 48 from Dopper data. In one embodiment, the same algorithm is applied. In alternative embodiments, the same algorithm with different parameters or a different algorithm is used to identify the lower border 50 from the B-mode or tissue data.

As shown, the border 50 farthest from the transducer is entirely different than the border 48 closest to the transducers. The borders 48, 50 are different if entirely different or if overlapping with some spatial difference.

In one embodiment, the borders 48, 50 of the vessel 44 are detected automatically by the processor 22 or other system component. A center of gravity of Doppler data is identified as an approximate center of the vessel or organ. Alternatively, the principle axis of inertia of the Doppler data is detected to determine an orientation of a vessel. The strongest borders closest to the approximate center are then identified. In alternative embodiments, the user assists in border detection by indicating one or more locations along the border 48, 50, indicating a portion of the vessel (e.g., an approximate center of the vessel in one, two or three dimensions), region of interest for border detection, or other input. For example, the user may alter a detected border.

In act 36, the detected borders 48, 50 are combined. The ordered list of spatial locations for the detected borders 48, 50 are associated spatially. The borders 48, 50 may also be combined with image data.

In act 38, calculations are performed as a function of the detected borders and/or images with the borders are generated. For example, a nearest or smallest distance between the top and bottom borders 48, 50 is calculated and used for volume flow measurements or estimating vessel diameter for endothelial function assessment. As another example, an area bounded by one or more borders is calculated. In addition or as an alternative, a graphic overlay representing the detected borders 48, 50 is generated and displayed. The graphic overlay is displayed alone or in combination with an image. For example, the graphic overlay is positioned on an image generated from the data used for detecting the border. The overlay is displayed on a B-mode, Doppler mode or combination B-mode and Doppler mode image. All or a subset of the detected borders are displayed with any of the various images.

The border detection process and systems discussed above can be used for imaging vessels, such as the brachial artery. In other embodiments, borders associated with organs, such as the heart or other fluid filled or fluid surrounded organs, are detected. Fluid and tissue data may be used for detecting different portions of any border. Organs or vessels associated with incomplete, noisy or reverberation artifact laden B-mode data may benefit from detecting a portion of the border from Doppler, fluid or flow data.

While the invention has been described above by reference to various embodiments, it will be understood that many changes and modifications can be made without departing from the scope of the invention. For example, data associated with different imaging techniques, such as MRI, CAT scan or X-ray, may be used. Acoustic or other contrast agents may be used to more accurately identify fluid or tissue data. Various data acquisition techniques may be used to obtain higher resolution tissue or fluid data, such as harmonic imaging or other techniques.

It is therefore intended that the foregoing detailed description be understood as an illustration of the presently preferred embodiments of the invention, and not as a definition of the invention. It is only the following claims, including all equivalents, that are intended to define the scope of the invention.

What is claimed is:

1. A method for detecting a border associated with a fluid region, the method comprising the acts of:
   (a) detecting a first portion of the border with Doppler data as a function of a prior identified tissue-to-fluid relationship of the first portion; and
   (b) detecting a second portion of the border with B-mode data as a function of a prior identified fluid-to-tissue relationship of the second portion, the second portion different then the first portion;
   wherein the tissue-to-fluid and the fluid-to-tissue are relative to a path of travel of ultrasound energy away from a transducer.

2. The method of claim 1 wherein (a) and (b) comprise detecting a two dimensional border of a vessel.

3. The method of claim 1 wherein (a) and (b) comprises detecting a three-dimensional border of a vessel.

4. The method of claim 1 wherein (a) comprises detecting the first portion in response to gradients associated with the Doppler data.

5. The method of claim 1 wherein (b) comprises detecting the second portion in response to gradients associated with the B-mode data.

6. The method of claim 1 wherein (a) comprises detecting the first portion in response to the Doppler data at a tissue-to-fluid border, and (b) comprises detecting the second portion in response to B-mode data at a fluid-to-tissue border, wherein the tissue-to-fluid and the fluid-to-tissue are relative to a path of travel of ultrasound energy away from a transducer.

7. The method of claim 1 further comprising:
   (c) separating the Doppler data and the B-mode data from combined image data.

8. The method of claim 1 further comprising:
   (c) displaying the first and second portions as an overlay on an image responsive to at least one of the B-mode and Doppler data.

9. The method of claim 1 further comprising:
   (c) positioning a transducer so that the first portion is closer to the transducer and the second portion is farther from the transducer.

10. The method of claim 1 wherein:
    (a) comprises detecting the first portion in response to gradients associated with the Doppler data, the first portion associated with a tissue-to-fluid border; and (b) comprises detecting the second portion in response to gradients associated with the B-mode data, the second portion associated with a fluid-to-tissue border, wherein the tissue-to-fluid and the fluid-to-tissue are relative to a path of travel of ultrasound energy away from a transducer; and further comprising:

(c) positioning a transducer so that the first portion is closer to the transducer and the second portion is farther from the transducer; and (d) displaying the first and second portions on an image responsive to at least one of the B-mode and Doppler data.

11. A system for detecting a border associated with a fluid region of a patient, the system comprising:

a first processor operable to detect a first portion of the border with fluid data and to detect a second portion of the border with tissue data, the second portion different then the first portion, the detection of the first and second portions based on identified relative distances from a transducer; and a second processor operable to combine the first and second portions of the border.

12. The system of claim 11 wherein the system comprises an ultrasound system, the fluid data comprises Doppler data and the tissue data comprises B-mode data;

further comprising a transducer operatively connected with the first processor.

13. The system of claim 11 wherein the first processor detects the first and second portions as a function of first and second gradients, respectively.

14. The system of claim 11 further comprising:

a memory for storing combined image data wherein the tissue and fluid data are obtained from the combined image data.

15. A method for detecting a border of a vessel, the method comprising the acts of:

(a) detecting the border of the vessel closer to a transducer with flow data; and (b) detecting the border of the vessel farther from the transducer with tissue data;

wherein act (a) is performed with the flow data based on the border of the vessel identified as being closer to the transducer, and act (b) is performed with the tissue data based on the border of the vessel identified as being farther from the transducer.

16. The method of claim 15 wherein (a) comprises detecting a top border of the vessel and (b) comprises detecting a bottom border of the vessel, the top and bottom borders being relative to the transducer.

17. The method of claim 15 wherein (a) comprises detecting the border closer to the transducer in response to gradients associated with ultrasound Doppler data; and (b) comprises detecting the border farther from the transducer in response to gradients associated with ultrasound B-mode data.

18. The method of claim 15 wherein (a) comprises detecting the border closer to the transducer at a tissue-to-fluid border, and (b) comprises detecting the border farther from the transducer at a fluid-to-tissue border, wherein the tissue-to-fluid and the fluid-to-tissue are relative to a path of travel of ultrasound energy away from the transducer.

19. The method of claim 15 further comprising:

(c) displaying the borders closer and farther from the transducer on an image responsive to at least one of the tissue and flow data.

20. The method of claim 15 further comprising:

(c) positioning the transducer so that the vessel is more parallel than perpendicular to a transmitting surface of the transducer.

* * * * *